United States Patent [19]

Gruber

[11] Patent Number: 4,593,046

[45] Date of Patent: Jun. 3, 1986

[54] METHOD OF REDUCING SKIN IRRITATION FROM BENZOYL PEROXIDE

[76] Inventor: Murray Gruber, 19 Laurel Dr., Great Neck, N.Y. 11021

[21] Appl. No.: 514,089

[22] Filed: Jul. 15, 1983

[51] Int. Cl.<sup>4</sup> ............................................ A61K 31/075
[52] U.S. Cl. .............................. 514/717; 424/DIG. 4; 514/844; 514/852; 514/859; 514/861; 514/864; 514/880; 514/886; 514/887
[58] Field of Search .................... 424/338, 62, 195; 514/714, 717, 783

[56] References Cited

U.S. PATENT DOCUMENTS 4,056,611 11/1977 Young .................................. 424/338
4,163,800 8/1979 Wickett et al. ....................... 424/62
4,178,372 12/1979 Coats .................................... 424/195

FOREIGN PATENT DOCUMENTS 0013459 7/1980 European Pat. Off. ............ 424/338

OTHER PUBLICATIONS

Cosmetics and Toiletries, 4/1980, vol. 95, Formula (42).

Primary Examiner—Dale R. Ore
Attorney, Agent, or Firm—Roberts, Spiecens & Cohen

[57] ABSTRACT

There is provided a dermatological composition for treating acne and similar skin lesions which comprises benzoyl peroxide and gel from the plant *Aloe vera*. The gel from *Aloe vera* helps to reduce specific undesirable reactions which would otherwise result from the use of benzoyl peroxide to treat skin lesions.

2 Claims, No Drawings

METHOD OF REDUCING SKIN IRRITATION FROM BENZOYL PEROXIDE

BACKGROUND OF INVENTION

This invention relates to dermatological preparations comprising aloe vera and peroxide compounds and processes for the conjoint use of such compositions. More particularly, the invention relates to topical medications for the treatment of skin blemishes and methods for treating skin lesions whereby the irritation commonly produced by peroxide compounds is ameliorated.

Acne and seborrhea are conditions of the human skin characterized by an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. When this normal sequence develops, hyperkeratinization of the follicular opening is stimulated, thus completely blocking the duct. The usual results are papules, pustules, or cysts, often contaminated with bacteria which cause secondary infections. Acne is characterized particularly by the presence of comedones, inflammatory papules, or cysts. The appearance of acne may range from slight skin irritation to pitting and even the development of disfiguring scars.

Many local therapeutic applications are utilized in the treatment of acne and seborrhea to prevent the obstruction of the follicular duct, to reopen the duct if it has become blocked to combat the infecting bacteria or the thickened sebum, and to provide combinations of each of these actions. The horny outer layer of the skin (stratum corneum) is formed of dead cells composed largely of keratin. Therapeutic agents which act to prevent the obstruction of the follicular duct by the removal or sluffing off of excess keratin are known as keratolytic agents. Salicylic acid, sulfur and resorcinol have been employed as keratolytic agents in the management of acne for at least 100 years.

Benzoyl peroxide has been employed as a keratolytic drug in the topical treatment of skin lesions such as acne, burns, varicose ulcers, sycosis vulgaris and seborrhea for the past sixty years. Benzoyl Peroxide $(C_6H_5CO)_2O_2$, is a colorless, odorless, tasteless, crystalline solid, stable at ordinary room temperatures; it is a powerful oxidizing agent, yet nontoxic to man. As previously mentioned, benzoyl peroxide has been employed as a very effective kerotolytic and antibacterial modality in the treatment of acne. While benzoyl peroxide is recognized by the F.D.A. as effective in concentrations of 2½%, 5% and 10% for the local treatment of skin lesions such as develop in acne or seborrhea, it has the adverse side effect of causing contact irritation. Accordingly, some patients are unable to derive the benefits peroxide acne therapy provides because of the irritation problem.

It has now been discovered that aloe vera blended with benzoyl peroxide even at 20% concentrations will reduce the skin irritations caused by the peroxide compound and enable the dermatologist to employ much more highly potent concentrations with superior clinical results and no more irritation and drying than with the F.D.A. approved 5% and 10%.

RELATED REFERENCES

When employed in the treatment of acne, benzoyl peroxide causes dryness, exfoliation and a decrease in the bacterial flora. The topical application of benzoyl peroxide in various greasy medicaments for the treatment of skin lesions such as burns, varicose, ulcers, sycosis vulgaris, and acne has been known for some years. Levine, et al Ohio State Med. J. 65,492 (1969). It is known that the employment of benzoyl peroxide in aqueous media in the form of lotions and gels (without the previously conventional presence of oils or fats as ointments and creams) provide very effective medical modalities for the treatment of acne and related conditions. Frank, L.: Active Oxygen in Acne Therapy, Cutis, 1:306-8, July 1965. Edelstein A. J.: Synergism in Recalcitrant Acne Vulgaris, Penn. Med., 69" 26-8, 1966. Frank, L. and Petrou, P.: Active Oxygen plus Chlorhydroxyquinoline in Acne and Pyodermas, Cutis, 3: 256-60, Jan. 1966. Witkowski, J. A. and Parish, L. C.: Chlorhdroxyquin-Benzol Peroxide Lotion in the Treatment of Acne, Cutis, 5: 1481-4, Dec. 1969. Ede, M.: A Double-Blind Study of Benzol Peroxide in Acne, Current Ther. Research, Vol. 15 #9, 624-9, 1973. Vasorinsh, P.: Benzol Peroxide-Sulfur Lotions, Cutis, 5:65-69, 1969.

Benzoyl peroxide formulations for the treatment of acne are disclosed in the following references; U.S. Pat. No. 3,535,422, Cox, et al., Oct. 20, 1970; British Pat. Nos. 1,185,685, Fisher, Mar. 25, 1970; 1,163,004 Stiefel Laboratories, Inc., Sept. 4, 1969; and 1,407,937 Stiefel Laobratories, Inc., Oct. 1, 1975.

The local application of benzoyl peroxide and benzoyl peroxide compositions for skin lesion therapy is thoroughly detailed in the medical literature, as is the associated irritation cuased by this substance. The efficiency of this drug and related unfavorable problems associated with its use, such as excessive drying, heavy scaling, edema, burning, peeling, redness, excessive erythema, allergic contact dermatitis, and sensitization reactions are discussed in the following references:

Brogdne, et al, Drugs, 8,417(1974); Poole, et al, Arch Derm; 102,400 (1972);

Eaglstein, Arch. Derm. 97,527 (1968); Pace, Can Med. Ass. J 93,252 (1965);

Vasarinsh, Arch. Derm. 98,183 (1968); Mysliborski, et et al, AFP 15, 86,(1977);

Hare, Br. J.Clin. Prac. 29,63 (1975); Fulton et al, Arch. Derm. 1 10,83(1974); and Wilkinson, et al., Can. Med. Ass. J. 95,28 (1966).

The U.S. Food & Drug Administration in recognition of these problems, limits the marketing of benzoyl peroxide products to a maximum of 10% concentration of this active ingredient and has classified higher potencies as new drugs with safety and efficacy not proven. The present invention enables the dermatologist to safely employ a much higher concentration of benzoyl peroxide without fear of these adverse side effects and with superior, more rapid therapeutic response by the patient.

Heretofore, a reduction in, or control of benzoyl peroxide irritation has been achieved by using certain gel and cream formations, or by temporarily suspending the application of the benzoyl peroxide compositions; Kulfik, et al., Cutis 17,175 (1976); Liddell, Br. J. Clin. Prac 28,379 (1974); and Kirton, Br. Clin. Prac 21, 127

(1976). U.S. Pat. No. 4,163,800 discloses the use of guanidine compounds to attempt to reduce or control benzoyl peroxide irritation.

As specified in the U.S. Pharmacopeia, "aloe is the dried latex of the leaves of *Aloe barbadensis* Miller (*Aloe vera* Linné), known in commerce as Curacao Aloe, or of *Aloe ferox* Miller and hybrids of this species with *Aloe africana* Miller and *Aloe spicata* Baker, known in commerce as Cape Aloe (Fam. Liliaceae)". The C.T.F.A. Cosmetic Ingredient Dictionary defines aloe as a plant material derived from the leaves of one or more species of Aloe and shows that it is also known as aloe vera.

Aloe vera has been well known and employed since ancient times. DIOSCORIDES recorded many uses of aloe, 2,000 I years ago both internally and externally. Amongst the indications he mentioned for topical application were hemorrhoids, itching, blistering, sunburn and skin blemishes.

Marco Polo found that the Chinese used aloe vera for the treatment of rashes and skin disorders.

More recently, additional uses for aloe vera were described; for example, U.S. Pat. No. 3,103,466 Farkas, Sept. 10, 1963 discloses the use of aloe vera to provide analgesic effect, quickly reducing pain while promoting granulation of the surface skin.

Antibacterial properties of aloe vera were disclosed by Lorenzetti, et al, J. Pharm. Sci. 53,1287 (1964), healing properties were disclosed by Brown, et al, Cancer Journal Clin. 14,15 (1963) anaesthetic and healing properties on burns and scales were disclosed by Crewe et al. Minn, Med. Aug. 1939, pp. 538 and Rovatti et al, Ind. Med. & Surg. August 1959 pp 36408. Efficacy of aloe vera in the treatment of leg ulcers and dermatoses was disclosed by El Zawahry, Int. J. Derm. Jan/Feb 1973, 68–74.

Successful treatment with aloe vera of the dermatitis which frequently developed due to excessive exposure of the skin to roentgen rays was disclosed by Collins, C. Collins, E; Am. J. Roentgen, Vol. 33, 1935 p. 396.

Advantageous treatment of roentgen radiation dermatitis with aloe vera has also been described by Brown, J. B., Cancer Journal for Clinicians, Vol, 14, pp. 14–15, 1963 as well as Lushbaugh, C. C. and Hale, D. B., Cancer, Vol. 6, pp. 690–698, July, 1953.

Aloe vera is also known to be useful in the treatment of burns and scales as noted by Crewe, J. E. Minn Med Aug. 1939, pp. 538–9, as well as Rovatti, R. and Brennan, R. J., Industrial Med. & Surg., Aug. 1959, pp. 364–8.

The chemistry of aloe vera has been investigated on and off during the past several decades. However, few of the studies have been well controlled or confirmed. Substances reported to occur in aloe vera include polysaccharides containing glucose, mannose, galactose, xylose, arabinose, tannins, steroids, organic acids, antibiotic principle(s), glucuronic acid, enzymes (oxidase, catalase and amylase), trace sugars, calcium oxalate, protein containing 18 amino acids, wound healing hormones, biogenic stimulators, saponin, vitamin chloride, sulfate, iron, calcium copper, sodium, potassium, manganese, etc.

It is commonly believed that the moisturizing emollient and healing properties of aloe vera are due to the polysaccharides present. The major polysaccharide present has been determined to be a flocomannan. Other polysaccharides containing galactose and uronic acids as well as pentoses are also present. It is probable that its beneficial properties are not due to the polysaccharides alone, but rather from a synergistic effect of these compounds with other substances present in the gel. Leun, A.; Effective Ingredients of Aloe Vera, Drugs & Cosmetics, June 1977, pp. 34–5 and 154–5.

Although aloe vera has been well known to be antibacterial and anaesthetic and, in certain instances, to relieve the symptoms of irritation, sting and burns, once they have occurred, nothing in the art would suggest the combination thereof with benzoyl peroxide to prevent the specific undesirable reactions which otherwise result from the use of benzoyl peroxide to treat skin lesions. None of the references suggest the use of a composite of benzoyl peroxide and aloe vera in the manner of the present invention.

SUMMARY OF THE INVENTION

It is an object of the invention to provide an improved dermatological composition.

Another object of the invention is to provide an improved method for treating severe acne and similar skin lesions and to obtain more rapid clinical results.

Yet another object of the invention is to prevent or reduce irritation resulting from contact of the skin with benzoyl peroxide.

To achieve the above and other objects of the invention, there is provided a dermatological composition comprising a keratolytically effective amount of benzoyl peroxide and an amount for reducing the skin irritation thereof of a substance or substances derived from speices of plants of the genus aloe and, preferably, from the species *Aloe vera*.

According to one specific embodiment of the invention, the substance may be the viscous gel of the internal portion of the leaf of the *Aloe vera*. The gel may be in the form of a liquid concentrate from which water has been removed from gel which has been freshly extracted from the leaf of *Aloe vera* and to which preservatives have been added to preserve the therapeutic qualities of the gel.

According to the invention, there is provided a method of treating skin lesions especially acne lesions by topically applying a safe and effective amount of peroxide compound to the afflicted situs in conjunction with gel from the plant *Aloe vera* whereby skin irritation caused by the peroxide compound is mitigated.

The above and other objects, features, and advantages of the invention will be found in the detailed description which follows hereinafter.

DETAILED DESCRIPTION OF THE INVENTION

The dermatological compositions herein comprise mixtures of toxicologically-acceptable peroxide compounds and toxicologically-acceptable aloe vera gel. These compositions are useful for the treatment of skin lesions, especially those of acne, with no more skin irritation than normally occurs when only the peroxide compounds are used. With applicant's new composition for the first time it is possible to prepare benzoyl peroxide at levels of 20%, or higher, for the treatment of severe acne when lesser concentrations of 5% and 10% have failed, without fear of tremendous irritation and dryness. In addition, the combination of benzoyl peroxide and aloe vera gel provides clinical results much more rapidly.

The compositions herein comprise a safe and effective amount of aloe vera gel and a safe and effective amount of peroxide compound, all as described more fully hereinafter. Said peroxide compounds can be used as microdispersions or as micro-suspensions in the form of micronized particles, said microns of peroxide being suspended in insoluble form in a suitable non-oily, non-greasy vehicle. Water is a pharmaceutically and cosmetically acceptable carrier.

As used herein the term "aloe vera gel" refers to gel from the "filet" of the leaves of the plant *Aloe vera*, and to such gel which has been stabilized to provide a durable perparation which preserves the therapeutic quality of freshly extracted gel, as will be set out more fully hereinbelow. The complete qualitative and quantitive chemistry of aloe vera gel has not been clearly defined and it is not a single chemical entity.

The leaves of the plant *Aloe vera* contain a viscous but essentially clear gel given structural rigidity by hairlike connective fibres that run through it. Freshly excised from the plant and applied to vitro, this gel has been used medicinally for centuries by those living where the plant normally grows to relieve the pain of plant and animal stings, such as jellyfish stings.

The clear gel of the *Aloe vera* is to be distinguished from the thick, mucilaginous yellow juice that occurs about the base of the plant leaves and adjacent to the rind of the leaf. This juice, known as aloin, has been used for many years as an ingredient in many carthartics and purges.

Since loss of the therapeutic qualities of the clear gel of the *Aloe vera* may occur due to aging or decomposition, gel which is freshly extracted from *Aloe vera* may be treated to make it a durable preparation. The gel from the plant *Aloe vera* is available and marketed commercially in different forms and with various additives to preserve the therapeutic qualities of the gel. For example, it is available as a so-called stabilized gel. The C.T.F.A. designation of aloe vera gel, stabilized, has the following physical and microbiological parameters:

| Appearance: | Clear to slightly lazy, yellow-green liquid |
| --- | --- |
| Gardner Color: | Maximum |
| Odor: | Aged vegetable/plant odor |
| Specific Gravity: | 0.980 to 1.000 @ 25° C. |
| pH: | 4.0–5.0 |
| Acid Value: | 2.0 |
| Refractometer: | (A.O. Model 10440): 1.0–2.0 |
| Microbiology: | Pathogenic organisms - Neg. 1 wk. Aerobic count less 10 cfu - 48 hours Mycology - CTFA standards - 1 week. |

Processes for the stabilization of the gel from the *Aloe vera* are known as is illustrated, for example, in U.S. Pat. No. 3,892,853. For example, stabilized gel may be prepared by the following process:

a. mechanically separating the nonbruised and non-discolored aloe vera gel matrix from the outer green cortex of the aloe vera leaf;

b. homogenizing said aloe gel matrix and adding a catalytic proportion of hydrogen peroxide thereto;

c. heating said gel containing said oxidant to a temperature within the range of from about 35° C. to about 80° C. for a sufficient time to cause said gel to assume a lighter appearance;

d. adding an effective proportion relative to said oxidant of a nontoxic antioxidant to stop catalytic oxidation; and e. adding an effective proportion relative to said antioxidant of a nontoxic buffer substance to maintain the pH of the gel solution at a value between pH 4 and pH 6.

The gel from the *Aloe vera* is also available commercially as a liquid concentrate. The gel as it comes from the leaf of the plant *Aloe vera* may comprise upwards of 99% of water. The gel may be made into a concentrate in which much of the water content is removed. The concentrate can be reconstituted by adding water to the concentrate to extend it to its "natural" state. Different suppliers sell aloe vera concentrates that vary in the amount of water needed to extend the concentrate to its "natural" state. Preservatives and antioxidants may also be added to these concentrates to preserve the therapeutic qualities of the gel.

By way of example of a liquid concentrate of aloe vera gel which may be used in the present invention, is a product designated "Aloe Vera Aqueous Extract Concentrate" available commercially from Terry Corporation of Melbourne, Fla. This product is a stabilized extract obtained only from the "filet" of the plant. It is processed to obtain a light yellow-green to amber translucent liquid with a viscosity slightly higher than water. It has a somewhat slippery feel. This product has the following specifications and use instructions:

| | |
| --- | --- |
| SPECIFICATIONS: | Physical State Opaque liquid<br>Color: Turbid off-white<br>Odor: Typical<br>Filterable Solids: @ ambient temperature and pressure through Tare Whatman #40 filter paper: <0.1% dry weight basis<br><br>Refractive Index: $\eta \frac{24}{D}$ 1.3529<br><br>Folin Wu Copper reducing substance: 2.75–3.5%<br>Specific Gravity: @ 25° C. 1.230–1.250<br>KOH presumptive test for Quinones: Positive<br>Constant Weight Residue @ 100° C.: 9.7–13.2%<br>pH: 4.1–4.8<br>Bacterial Count: 10/gram |
| PRESERVATIVES AND ANTIOXIDANTS | 2-Bromo-2-Nitropropane-1, 3-Diol: Not greater than 0.2%<br>Residual Process Formaldehyde: Not greater than 0.15%<br>Propyl Gallate: Not greater than 0.01% |
| OTHER ANALYSIS FOR RANDOM SELECTED ALOE VERA AQUEOUS EXTRACT(S) BELIEVED TO BE TYPICAL: | Copper: Circa 0.0003%<br>Lead: Circa 0.00006%<br>Potassium: Circa 0.035%<br>Sodium: Circa 0.009%<br>Aluminum: Circa 0.004%<br>Calcium: Circa 0.0122%<br>Mercury: Less than 0.000005%<br>Average % volatiles of constant weight solids (@ 100° C.) Circa 95.6%<br>Typical Freeze Point: <−2° C.<br>Typical Boiling Point: >103° C. |
| RECOMMENDED USE AND EXTENSION METHODS: | Aloe Vera Aqueous Extract Concentrate should normally be extended 1/9 v/v (i.e. one (1) part of Aloe Vera Aqueous Extract Concentrate to nine (9) parts by volume of distilled or demineralized water (or if desired alcohol) prior to use in desired product.<br>In no instance should the Concentrate be used in amounts greater than 10% of the aqueous and/or alcohol content of the finished product.<br>To produce crystal clear alcohol compound the Concentrate should be added to 3–4 volumes of alcohol, mixed and allowed to stand at room temperature for about thirty minutes then filtered and the filtered solution then extended to proper volume with the additional required alcohol or water. |

| | |
|---|---|
| | Typically, most users have found the most efficacious product percentage of Aloe Vera Aqueous Extract Concentrate (1/9 v/v) to range between 5 and 25% of the finished product. |
| STORAGE: | Aloe Vera Aqueous Extract Concentrate should be stored in clean cool area. Prolonged storage at temperatures above 147° F. (63.9° C.) should be avoided. Product is not adversely affected by freezing so long as container remains undamaged. Product may be stored in its original unopened, undamaged container for more than three years without loss of efficacy. |

As used herein, the term "Aloe Vera Aqueous Extract Concentrate" refers to a liquid concentrate of aloe vera gel which has been made into a stable preparation, a representative sample of which is the product available from Terry Corporation.

The term "peroxide compounds" as used herein encompasses compounds of the formula $R_1$—O—O—$R_2$ where $R_1$ and $R_2$ are hydrogen or organic substitutes. The preferred peroxide compound is benzoyl peroxide.

By "safe and effective amount of aloe vera gel" herein is meant a sufficient amount of said compound to reduce skin inflammation, irritation, peeling, flaking and other adverse effects resulting from the use of peroxide compounds, especially benzoyl peroxide. The amount of aloe vera gel incorporated will vary with the particular condition being treated, the severity of the condition, the duration of the treatment, the percentage of benzoyl peroxide employed and its usage concentration, the severity of the reaction to the peroxide compound, and like factors within the specific knowledge and expertise of the attending physician.

By "safe and effective amounts of peroxide compound" herein is meant a sufficient amount of said peroxide compound to alleviate skin lesions at a reasonable benefit/risk ratio attendant with any medical treatment. Within the scope of sound medical judgement, the amount of peroxide compound used will vary with the particular condition being treated, the severity of the condition, the duration of the concentration of benzoyl peroxide employed, and like factors within the specific knowledge and expertise of the attending dermatologist.

By "toxicologically or pharmaceutically acceptable" herein is meant ingredients which are suitable for use in contact with the tissues of humans and lower animals without undue toxicity, irritation, allergic response, and the like, commensurate with a reasonable benefit/risk ratio.

By the term "comprising" herein is meant that various other compatible drugs and medicaments, as well as inert ingredients and cosmetic vehicles, can be conjointly employed in the compositions and processes of this invention, as long as the critical aloe vera gel and benzoyl peroxide compounds are used in the manner disclosed. The term "comprising" thus encompasses and includes the more restrictive terms "consisting of" and "consisting essentially of" which characterized the use of the essential ingredients in the manner disclosed herein.

By "applying topically" herein is meant directly laying on or spreading on epidermal tissue, especially outer skin.

By "afflicted situs" herein is meant a localized area of inflammation or lesions, and the immediate surrounding area.

By "skin lesion" herein is meant macules, patches, papules, plaques, nodules, comedones, burns, varicose and other skin ulcers, seborrhea, sycosis vulgaris, pustules, cysts and similar afflictions treated medically by the application of peroxide compounds.

By "acne" herein is meant common acne, acne vulgaris, in all forms including papuler, pustular or cystic.

By "in conjunction with" herein is meant application of the aloe vera gel either before, after, or at the same time as the application of the peroxide compound.

By "treating" herein is meant the topical use of the compositions herein on an afflicted situs and the process of topically applying an aloe vera gel compound in conjunction with a peroxide compound to an afflicted situs.

By "particulate" herein is meant particles of the benzoyl peroxide compound within a size range below a diameter of about 0.1 mm. Particles below a diameter of about 0.05 mm are said to be "impalpable", inasmuch as they cannot be felt and recognized as particles on the skin of the average user and are preferred for use herein.

As used herein, the terma microdispersion and microsuspension are interchangeable. Both mean the dispersion and permanent suspension of minute particles, below a diameter of 0.1 mm. in a pharmaceutical system, i.e. lotions, creams, liquids, shampoos or similar forms in which the particles do not "settle out" or form conglomerates, clumps or precipitates.

In addition to the aloe vera gels and benzoyl peroxide compounds, the compositions described herein can include any cosmetic vehicle which does not react with aloe vera gel or the peroxide compound. Other ingredients can be included in the compositions to provide aesthetic and cosmetic benefits and to facilitate use. Several of these are also disclosed hereinafter. All percentages herein are by weight, unless otherwise specified. Typical compositions may include less desirable emollients such as hydrocarbon oils, and waxes, lanolin and lanolin derivatives, silicone oils, triglyceride-esters, fatty acids, fatty alcohols, alkyl and alkenyl esters of fatty acids, polyhydric alcohols and polyether derivatives, wax esters and beeswax derivatives. Such emollients preferably comprise from 10% to 50% of the compositions.

More desirable emulsifiers of the nonionic, anionic, or cationic classes can also be used, and will usually comprise from 1% to 10% of the composition. Suitable emulsifiers include nonionic emulsifiers such as fatty acid monoglycerides, fatty alcohols, polyethylene glycols, and propylene glycols, anionic emulsifiers, such as alkyl ethoxy ether sufonates, ammonium alkyl sulfates, and fatty acid soaps, and cationic emulsifiers such as quaternary ammonium, morpholinium and pyridinium compounds. When an emollient which has emulsifier properties is used, less additional emulsifier is necessary.

Chelating agents such a EDTA, nitrioltriacetate and gluconic, citric, and tartaric acids, preferably at a level of from 0.1% to 1% of the composition, may be used to avoid the decomposition of the peroxide compound by metal ions.

Optional components such as finely divided sulfur, USP grade, at a level of from 1% to 25% of the composition, thickening agents, such as cross-linked carboxyl polymethylene polymers, bentonite, gum tragacanth, grum kharava, and polyethylene glycols, at a level from 1% to 10% of the composition, and trace amounts of fragrance materials such as perfumes can also be used. The balance of the composition may comprise water with or without acetone or alcohol.

The compositions are typically prepared by thoroughly blending all of the components together in admixture and milling, if necessary, to reduce all particles to impalpable size. The benzoyl peroxide should be of high purity, on the order of 97% to 100% pure and in the form of finely divided powder. The powder may be either wet or dry, but is preferably wet for ease of handling and safety. If wet benzoyl peroxide is used, it may be necessary to grind the crystals before admixture or to mill the composition after admixture and blending to reduce the crystals to impalpable size. Preferably, the milling or grinding operation is performed in the cold to prevent decomposition of the peroxide by localized friction.

Aloe vera gel when freshly processed ranges in pH from 4.5 to 5.5 and the enzyme cellulose is present in the resultant gel. Accordingly, the pH of the current invention may be adjusted to pH 5.5 and gum like cellulose derivative thickeners such as methyl cellulose cannot be employed. Accordingly, carbomers which do not affect the cellulose may be utilized as thickening agents.

The following examples illustrate the present methods and compositions, but are not intended to be limitations thereof. The compositions are typically applied twice daily to acne lesions. The typical usage rate is about 0.001 g/cm$^2$ skin to about 0.5 g/cm$^2$ skin per application but this can vary with the user, the severity of the affliction, and the concentrations of aloe vera gel and peroxide compound in the particular composition being used.

EXAMPLES

Combinations of aloe vera gel with 20% benzoyl peroxide in one composition were made in the manner shown hereinbelow. The aloe vera gel used was Aloe Vera Aqueous Extract Concentrate (AVAEC) as supplied by Terry Corporation of Melbourne, Fla. The other components of the embodiments below, except for water and benzoyl peroxide, are optional—they are not essential to the invention.

| EXAMPLE I | A | Carbomer 940 | 1.5% |
|---|---|---|---|
| | | Purified Water | 49.0% |
| | | Laureth 4 | 5.0% |
| | | Benzoyl Peroxide | 20.0% |
| | | Propylene Glycol | 5.0% |
| | B | Triethanolamine | 1.5% |
| | | Purified Water | 8.0% |
| | C | Acetone | 10.0% |
| | | AVAEC | 0.1% to 2.5% |
| | | Directions for Manufacture. | |
| | 1. | Admix all items in A. Blend this portion in a roller mill until all particles are eliminated and the composition is impalpable. | |
| | 2. | Admix triethanolamine and water and add to A. | |
| | 3. | While mixing A & B, slowly add the acetone and finally the AVAEC. | |
| EXAMPLE II | A | Carbomer 940 | 1.3% |
| | | Purified Water | 49.0% |
| | | Glycerine | 8.0% |
| | | Benzoyl Peroxide | 20.0% |
| | | Polysorbate 80 | 3.0% |
| | B | Diethanolamine | 1.3% |
| | | Purified Water | 10.0% |
| | C | Ethyl Alcohol | 8.0% |
| | | AVAEC | 0.1% to 2.5% |
| | | Directions for Manufacture Same as in Example I | |
| EXAMPLE III | A | Carbomer 941 | 1.4% |
| | | Purified Water | 42.0% |
| | | Gum Tragacanth | 1.0% |
| | | EDTA | 0.5% |
| | | PEG 400 | 4.0% |
| | | Propylene Glycol | 8.0% |
| | | Benzoyl Peroxide | 20.0% |
| | B | Ethomeen C 25 | 1.4% |
| | | Purified Water | 10.0% |
| | C | Sorbitol | 12.0% |
| | | AVAEC | 0.1% to 2.5% |
| | | Directions for Manufacture Same as in Example I | |
| EXAMPLE IV | A | Acidified collodial magnesium aluminum silicate gel in purified water | 61.0% |
| | | Purified Water | .% |
| | | Laureth 4 | 6.0% |
| | | EDTA | 0.5% |
| | | Benzoyl Peroxide | 20.0% |
| | | Propylene Glycol | 6.0% |
| | B | Alcohol | 6.0% |
| | | AVAEC | 0.1% to 2.5% |
| | | Directions for Manufacture. | |
| | 1. | Prepare a gel comprising 61% of the total formulation with Magnesium aluminum silicate. Blend this portion in roller mill until all particles are eliminated and the composition is impalpable. While | |
| | 2. | mixing slowly add the alcohol and AVAEC phase. | |

An evaluation of the composition produced according to the instant invention was made in the manner and with the results shown below.

COMPARISON STUDIES

I. Clinical Evaluation

Commercially available benzoyl peroxide medications are limited by U.S. Federal law, for the treatment of acne, to a maximum level of 10% potency because of the known accompanying disadvantageous and undesirable burning, irritation and other adverse reactions which often accompany its use. The subject composition was tested against 10% Benzoyl Peroxide Gel which did not contain AVAEC in a series of double-blind studies and was proven to provide more rapid and superior therapeutic effects and to cause less problems in acne patients than a commercially available and frequently employed 10% Benzoyl Peroxide Gel (Panoxyl 10% Gel supplied by Stiefel Labs of Oakhill, N.Y.) without AVAEC.

II. Animal Dermal Studies a. A topical application study on guinea pigs was conducted in order to evaluate the potential for dermal irritation of this composition by comparison with Panoxyl 10% Gel. The results of this study revealed a 20% benzoyl peroxide composition of the instant invention was in many instances less and was in no instance more irritating than the 10% benzol peroxide gel.

b. A study on guinea pigs was conducted in order to evaluate the potential for dermal irritation of the 20% benzoyl peroxide gel by comparison with Transact gel, available commercially from Westwood of Buffalo, N.Y. This is a widely advertised and sold over-the-counter acne product containing 2% sulfur in gel form. The results demonstrated that a 20% benzoyl peroxide composition of the instant invention was significantly less irritating than the 2% sulfur gel. Both, however, were found to be within acceptable levels for acne medications of this nature.

III. Ocular Irritation Study

A study on rabbits was conducted to evaluate the potential for ocular irritation of this composition as compared with Panoxyl 10% Gel, available from Steifel Labs. Each of the compositions was instilled in rabbit eyes in exactly the same concentration employing the same procedures. Both were irritating but at the end of the 7 days there was no evidence of irritation with a 20% benzoyl peroxide composition of the instant invention while there was significant irritation at the end of this period with the 10% commercial benzoyl peroxide gel.

IV. Feeding Study

A massive dosage feeding study was conducted on rats. A composition of benzoyl peroxide with Aloe Vera Aqueous Extract Concentrate was found to be absolutely non-toxic.

V. Human Dermal Study

Forty-eight hour occlusive patch tests were made on humans. A 20% benzoyl peroxide composition of the instant invention was applied to the left forearm and a 10% benzoyl peroxide gel without aloe vera was applied to the right forearm. All patches of both products evinced some erythema but the 10% benzoyl peroxide gel reaction was more marked than the 20% benzoyl peroxide composition containing AVAEC. In no instance was an allergic reaction observed.

VI. Human Hematology Study

Laboratory studies of complete blood count with differential urinalysis with microscopic, and the following chemistry tests were performed: SGOT, Alkaline Phosphatase, Bilirubin, Greatinine, BUN.

The results showed that the topical application of 10% and 20% Benzoyl Peroxide caused no significant changes in the laboratory parameters employed in this evaluation.

VII. Stability Study

Stability studies on the subject composition were conducted on a continuing basis fof 36 months. These studies included integrity, appearance, odor consistency, pH weight loss and cycling. The studies demonstrated acceptable pharmaceutical stability of the subject composition for at least 36 months.

The double strength of benzoyl peroxide in the subject composition has been not only proven stable in this vehicle, but the irritation potential has been proven markedly reduced or eliminated by the conjoint presence of the aloe vera.

Accordingly, in this combination, the concomittant presence of AVAEC makes it possible to ameliorate the inherent irritancy potential of benzoyl peroxide so that high concentrations of the drug can be safety employed for severe acne and for more rapid therapeutic effect without undue concern about unacceptable and excessive skin irritation. It is obvious that the AVAEC would also serve to reduce possible irritation and redness if incorporated in 5% and 10% benzoyl peroxide as well.

The present invention enables a dermatologist to safely employ a much higher concentration of benzoyl peroxide without fear of adverse side effects and with superior, more rapid therapeutic response by the patient than was heretofore possible. In addition, severe acne involvement which does not respond to 10% benzoyl peroxide applications frequently regress when the present invention which may, for example, encompass compositions of matter comprising mixtures of AVAEC up to 15% and benzoyl peroxide gels up to 25% compounded in pharmaceutically suitable vehicles such as gels and lotions, are employed. Potencies up to 25% of peroxides can exert their keratolytic, antibacterial, antiseborrheic, healing action, while the AVAEC exerts its assuasive action so that the irritating, burning, stinging sensation which often accompanies the prolonged application of even 5% of benzoyl peroxide and other peroxides are significantly reduced and often eliminated completely. The surprising advance in the therapy assures patient co-operation and consequently superior therapeutic results.

As can be seen from the foregoing, compositions of the present invention comprising AVAEC and a peroxide, conveniently at a weight ratio in the range of about ½% to 25% and preferably 1% to about 3% provided excellent therapy for acne and the like diseases.

There will now be obvious to those skilled in the art are many modifications and variations of the methods and compositions set forth hereinabove. These modifications and variations will not depart from the scope of the invention if defined by the following claims.

What is claimed is:

1. A process for reducing the skin irritation resulting from contact of the skin with benzoyl peroxide wherein the aloe vera gel and the benzoyl peroxide are admixed together prior to applying to the skin of a patient and wherein the admixture of aloe vera gel and benzoyl peroxide comprises at least about 20% wt. of benzoyl peroxide and at least about 0.1% of aloe vera gel.

2. A process as claimed in claim 1, wherein the aloe vera gel is applied in an amount of between 0.1% and 2.5% by weight of a concentrate of aloe vera gel.

* * * * *